United States Patent
Pucci et al.

(10) Patent No.: US 8,642,309 B2
(45) Date of Patent: Feb. 4, 2014

(54) POLYMERS COMPRISING A MAJORITY OF AMPHIPHILIC MONOMERS INTENDED FOR TRAPPING AND MANIPULATING MEMBRANE PROTEINS

(75) Inventors: Bernard Pucci, Molleges (FR); Fabrice Giusti, Sceaux (FR); Paola Bazzacco, Paris (FR); Jean-Luc Popot, Paris (FR); Sharma Kshatrapati Shivaji, Majra (IN); Gregory Durand, Villeneuve les Avignon (FR)

(73) Assignees: Centre National de la Recherche Scientifique (CNRS), Paris (FR); University d'Avignon et des Pays de Vaucluse, Avignon Cedex (FR)

( * ) Notice: Subject to any disclaimer, the term of this patent is extended or adjusted under 35 U.S.C. 154(b) by 0 days.

(21) Appl. No.: 13/509,853

(22) PCT Filed: Nov. 16, 2010

(86) PCT No.: PCT/EP2010/067609
§ 371 (c)(1),
(2), (4) Date: Aug. 31, 2012

(87) PCT Pub. No.: WO2011/058195
PCT Pub. Date: May 19, 2011

(65) Prior Publication Data
US 2013/0005016 A1 Jan. 3, 2013

(30) Foreign Application Priority Data
Nov. 16, 2009 (FR) ...................................... 09 58072

(51) Int. Cl.
*C08F 24/00* (2006.01)
*C08L 89/00* (2006.01)
*C12N 11/04* (2006.01)

(52) U.S. Cl.
USPC ...... 435/182; 525/54.1; 524/498; 526/238.23

(58) Field of Classification Search
None
See application file for complete search history.

(56) References Cited

FOREIGN PATENT DOCUMENTS

| | | |
|---|---|---|
| FR | 2873123 | 1/2006 |
| WO | 9010023 | 9/1990 |
| WO | 9827434 | 6/1998 |
| WO | 2008058963 | 5/2008 |

OTHER PUBLICATIONS

Sharma et al., "Glucose-based amphiphilic telomers designed to keep membrane proteins soluble in aqueous solutions: synthesis and physicochemical characterization," Langmuir (2008) 24(23):13581-13590.

Tribet et al., "Amphipols: polymers that keep membrane proteins soluble in aqueous solutions," Proc Natl Acad Sci USA (1996) 93(26):15047-15050.

Prata et al., "Non-Ionic amphiphilic polymers derived from Tris(hydroxymethyl)-acrylamidomethane keep membrane proteins soluble and native in the absence of detergent," Biopolymers (2001) 56:77-84.

*Primary Examiner* — Lisa J Hobbs
(74) *Attorney, Agent, or Firm* — Pepper Hamilton LLP

(57) ABSTRACT

The invention relates to an amphiphilic polymer comprising at least 75% of amphiphilic monomers of formula (I), the average molar mass of the polymer being between 800 and 100 000, and also water-soluble complexes between the polymer according to the invention and a hydrophobic or amphiphilic compound, in particular a membrane protein, a concentrated aqueous solution of one or more such complex(es), a product comprising one or more such complex(es) attached to a substrate by means of the polymer according to the invention, and various uses of these products.

19 Claims, 2 Drawing Sheets

| Complexes | tOmpA/APol ratio | Ve (ml) | HHW (ml) | Peak |
|---|---|---|---|---|
| tOmpA/SS174 | 1:10 | 12.6 | 0.89 | right |
| tOmpA/SS174 | 1:4 | 12.2 | 1.13 | central |
| tOmpA/A8-35 | 1:4 | 11.9 | 1.00 | left |

US 8,642,309 B2

POLYMERS COMPRISING A MAJORITY OF AMPHIPHILIC MONOMERS INTENDED FOR TRAPPING AND MANIPULATING MEMBRANE PROTEINS

FIELD OF THE INVENTION

The invention relates to amphiphilic polymers useful for the manipulation of hydrophobic compounds in aqueous solution, water-soluble complexes formed between hydrophobic compounds, in particular membrane proteins, and said polymers, methods for preparing said complexes, and the applications of said complexes, particularly to diagnostic or analysis methods.

PRIOR ART

Integral membrane proteins, a particular class of proteins, are inserted in vivo into biological membranes, the double lipidic layer of which they pass through. The surface of these proteins coming naturally into contact with the membranes (transmembrane areas) is particularly hydrophobic, the extramembrane surfaces being, for their part, mainly hydrophilic. Membrane proteins ensure essential biological functions, particularly as regards exchanges of information or molecules between the various cell compartments and between the cell and its environment.

In this respect, membrane proteins have a major interest in the medical field. They represent, for example, privileged targets for medicinal molecules. They are also involved in numerous human illnesses, certain of which (for example multiple sclerosis or *myasthenia gravis*) have an autoimmune component manifested by the presence in the serum of autoantibodies directed against membrane proteins.

The manipulation in aqueous solution of membrane proteins is usually an indispensable prerequisite to their purification and to their structural and functional study. It necessitates avoiding the spontaneous aggregation of the hydrophobic domains and, to this end, maintaining around the transmembrane areas an amphiphilic environment.

Conventional preparations of such proteins in the water soluble state contain supramicellar concentrations of particular surfactants, detergents. The success of the method is based on the adsorption, on the transmembrane protein regions, of these amphiphilic compounds and dispersants. The manipulation of the complexes thereby formed is nevertheless much more delicate than that of soluble proteins, precisely on account of the presence of detergent. This must be present at a concentration greater than its critical micelle concentration (cmc) in all of the solutions containing the studied protein. Apart from possible problems of cost posed by the consumption of detergent, the experiments are often rendered delicate on account of the fact that the membrane proteins are usually unstable in detergent solution. Thus, in the presence of an excess of micelles, they have a tendency to irreversibly denature, whereas a surfactant defect leads in general to their precipitation.

This situation has led to the search for alternatives to the use of detergents, among which will be cited for example bicelles, which are small lipidic discs stabilised by surfactants, nanodiscs, the structure of which is similar but where the surfactant is a protein, peptitergents, which are amphiphilic peptides, lipopeptides, also peptidic but bearers of hydrocarbon chains, fluorinated or hemifluorinated surfactants, and amphipols, to the family of which belong molecules forming the subject matter of the present patent application.

Amphipols are amphiphilic polymers specially designed to replace detergents at the transmembrane surface of membrane proteins (Tribet et al, WO 1998/027434). This patent describes the use of co-amphiphilic polymers for maintaining membrane proteins in aqueous medium.

Most amphipols or so-called molecules as described to date are ionic polymers, in particular anionic, which prohibits their use in various analytical (isoelectrofocalisation) or separation (chromatography on ion exchange column) systems, and it is not a factor favourable to the crystallisation of the membrane proteins thereby stabilised. There thus exists a need for amphiphilic polymers having the advantages of existing amphipols for the manipulation of membrane proteins and which would be non ionic.

Non ionic amphipols have been described in Prata et al and Sharma et al. In Prata et al, the amphipols are copolymers comprising two types of monomers (see FIG. 2 of this document), one hydrophilic (2 OH and 1 sugar or 3 OH) and the other amphiphilic (2 OH and a fatty chain). In this document, the molar ratio between the hydrophilic monomers and the amphiphilic monomers has been maintained between 3.0 and 6.7, which corresponds to 75-87% of hydrophilic monomers and 13-25% of amphiphilic monomers, which are thus the minority.

In Sharma et al, amphipols are copolymers comprising two types of monomers (see Schema 1 of this document), one hydrophilic (2 OH and 1 sugar) and the other amphiphilic (1 OH, 1 sugar and one fatty chain). In this document, the molar ratio between hydrophilic monomers A and amphiphilic monomers B was maintained between 3 and 5, which corresponds to 75-83% of hydrophilic monomers A and 17-25% of amphiphilic monomers B, which are thus the minority. This is explained by the fact that the authors have noted that the amphipol comprising the highest percentage (25%) of amphiphilic monomers already had a reduced aqueous solubility.

Patent application WO 2008/058963 describes the immobilisation of membrane proteins on supports by means of amphipols which are copolymers comprising different types of monomers (hydrophilic, amphiphilic or hydrophobic), in which the ratio of the total percentage of hydrophobic or amphiphilic monomers over the total percentage of hydrophilic monomers is comprised between 0.25 and 2.5 (see claim 3 of WO 2008/058963). The exemplified amphipol is an ionic copolymer comprising hydrophilic monomers and hydrophobic monomers (see FIG. 1A of this document). In addition, the groups defined as amphiphilic in this application comprise hydrophilic and hydrophobic functions mixed within the same "graft", and not separate hydrophilic groups and hydrophobic groups, grafted separately onto the side chain.

Thus, all of the amphipols or so-called molecules as described to date are copolymers, comprising units of different properties, some hydrophilic, others hydrophobic and/or amphiphilic, the amphiphilic monomers being in the minority when they are present.

Moreover, the results presented in Sharma et al suggest that it is necessary to include hydrophilic monomers in addition to amphiphilic monomers, in order to conserve a sufficient aqueous solubility of the amphipols.

However, the copolymeric structure of all the molecules described to date has an important drawback: it makes it difficult to reproduce exactly the same chemical structure from one batch to the next. The synthesis in fact requires either a radical copolymerisation, or a random functionalisation of a homopolymer type precursor, two types of non selective reactions in essence. There thus exists a need for amphiphilic polymers having the same advantages for the manipulation of hydrophobic compounds, and membrane proteins in particular, than those of the prior art, and the preparation of which would be much more reproducible from one batch to the next.

DESCRIPTION OF THE INVENTION

Unlike what is suggested in Sharma et al (4), the inventors have shown in a surprising manner that homoamphiphilic polymers (homoAPols) constituted of amphiphilic monomers, or copolymers comprising a large majority of such amphiphilic monomers ("quasi-homopolymers") can have a sufficient solubility in water to enable the manipulation of membrane proteins as well as the copolymeric amphipols known in the prior art. Moreover, these homopolymers or quasi-homopolymers can be manufactured in an entirely reproducible manner and thus do not have the drawbacks of the copolymeric amphipols known in the prior art.

The present application thus relates to an amphiphilic polymer comprising at least 75%, at least 80%, advantageously at least 85%, at least 90%, at least 95%, at least 96%, at least 97%, at least 98%, at least 99%, or even 100% of amphiphilic monomers of formula (I):

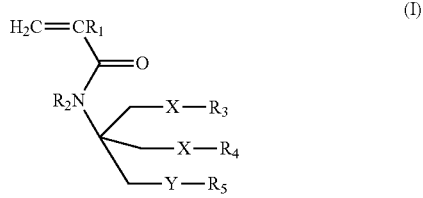

in which $R_1$ and $R_2$ are independently selected from H or a $C_1$-$C_3$ alkyl group (preferably a methyl);

X and Y are independently selected from an oxygen atom, a sulphur atom, a carbonyloxy (—(CO)O—) or oxycarbonyl (—O(CO)—) group, a urethane group (—OCONH—), and an amide group of formula (—CONR$_6$—) or (—NR$_6$CO—) wherein R$_6$ is a hydrogen atom or a $C_1$-$C_6$ alkyl, (preferably a methyl or an ethyl);

R$_3$ and R$_4$ are independently selected from:
a) glycosidic groups,
b) zwitterionic residues,
c) poly(oxyalkylene) groups of formula -(0(CH$_2$)$_x$)$_y$—OH, wherein x is comprised between 1 and 6 (advantageously x is equal to 2) and y is comprised between 4 and 30, advantageously between 4 and 20 or between 4 and 10,
d) alkylamide groups of formula —(CH$_2$)$_n$CONR$_7$R$_8$ or —(CH$_2$)$_n$NR$_7$COR$_8$ wherein n is comprised between 1 and 4, R$_7$ and R$_8$ are selected independently from a hydrogen atom (—H), a $C_1$-$C_6$ alkyl group (preferably a methyl), a glycosidic group, a zwitterionic residue or a poly(oxyalkylene) group of formula —(O(CH$_2$)$_x$)$_y$—OH wherein x is comprised between 1 and 6 (advantageously x is equal to 2) and y is comprised between 4 and 30, advantageously between 4 and 20 or between 4 and 10, R$_5$ is a cyclic (R$_5$ may contain one or two cycles, saturated or not, particularly of cyclohexane, cyclopentane or aromatic type) or acyclic (linear or branched), saturated or unsaturated (one or more unsaturations), hydrocarbon chain comprising from 5 to 16 atoms of carbon, or a hemifluorocarbonated chain of formula $C_tF_{2t+1}(CH_2)_m$ with t comprised between 2 and 10 and m comprised between 2 and 10, the average molar mass of the polymer being comprised between 800 and 100 000, which corresponds to a number of monomers comprised between 1 and 120, advantageously less than or equal to 50 000, preferably between 8000 and 50 000. The average molar mass is given by weight.

"$C_x$-$C_y$ alkyl" is intended to mean a saturated hydrocarbon radical, linear or branched, of formula —$C_jH_{2j+1}$, wherein x≤j≤y. Particularly, a $C_1$-$C_6$ alkyl may be a $C_1$ (methyl), $C_2$ (ethyl), $C_3$ (n-propyl, or isopropyl), $C_4$ (n-butyl, isobutyl, sec-butyl or tert-butyl), $C_5$ (e.g.: n-pentyl, neopentyl, isopentyl, tert-pentyl) or $C_6$ (n-hexyl for example) alkyl.

When the polymer according to the invention comprises other monomers than those of formula (I), said monomers are monomers with an acrylic or vinylic function with a side chain substituted by a hydrophilic or hydrophobic group. In particular, the hydrophilic or hydrophobic groups of the side chains may be selected from those defined in claims 3 and 4 of the publication PCT WO 2008/058963, the content of these claims being incorporated by reference.

Advantageously, R$_1$ and R$_2$ are independently selected from H or a methyl group. More advantageously, R$_1$ and/or R$_2$ are a hydrogen atom.

Also advantageously, X is an oxygen atom.

Also advantageously, Y is a urethane group (—OCONH—).

"Glycosidic group" is intended to mean any group comprising a sugar. The advantageous glycosidic groups for R$_3$ and/or R$_4$ are in particular:
mono- or di-saccharides, or
aminated mono- or di-saccharides.

"Monosaccharide" or "simple sugar" is intended to mean a non hydrolysable carbohydrate monomer. Advantageously, the monosaccharide is selected from hexoses (simple sugars with 6 carbon atoms), particularly from glucose, mannose, galactose, allose, altrose, idose, or maltose.

"Disaccharide" or "diose" is intended to mean a sugar formed of two simple sugars bonded by an osidic bond hydrolysable by chemical route (use of hot concentrated acids) or by enzymatic route. Advantageously, the disaccharide is selected from dihexoses, formed of two hexoses, such as lactose (Galactose β(1→4) Glucose), cellobiose (Glucose β(1→4) Glucose) or maltose (Glucose α(1→4) Glucose).

"Polysaccharide" is intended to mean a sugar constituted of a linear or branched polymer, composed of at least 2 monomers selected from the monosaccharides as defined above and which can reach 20 units, such as certain amyloses. The term polysaccharide thus includes disaccharides (or dioses), trisaccharides (or trioses), etc. up to 20 monosaccharide units. Preferably, the monosaccharide units are hexose units as defined above.

"Aminated mono-, di-, or poly-saccharide" is intended to mean any monosaccharide, disaccharide or polysaccharide as defined above in which one or more alcohol functions (—OH) has/have been substituted by an amine (—NH$_2$). Glucosamine, galactosamine, fructosamine, or mannosamine may be cited as examples of aminated monosaccharides, and aminolactitol as an example of di-saccharide.

Mono- or di-saccharides are particularly preferred, in particular mono- or di-hexoses of glucose, mannose, galactose, lactose, allose, altrose, idose, lactose, maltose, or cellobiose type; glucose, mannose and galactose being particularly preferred, especially glucose.

These glycosidic groups are grafted, in particular when X is an oxygen atom, either via the oxygen of the anomeric carbon (O glycosylation), or via that of the primary hydroxyl (ester bond) or via the aminated function (amide bond), or finally via the nitride group in which the anomeric carbon will have been provided beforehand in substitution of the hydroxyl group. In the latter case, the sugars are introduced by means of the Huygens reaction on a propargyl function grafted beforehand onto the X function, which will in this particular instance be an oxygen atom. Advantageously, the glycosidic group is grafted via the oxygen of the anomeric carbon (O glycosylation)

"Zwitterionic residue" is intended to mean a group having formal electric charges of one unit, of opposite signs and situated in general on non adjacent atoms. These compounds have at the same time positive and negative charges, they are highly soluble in water, which is a polar solvent. Advantageous zwitterionic residues stem for example from simple betaines (particularly of $-N^+(CH_3)_2C(CH_2)_iCO_2^-$, $-N^+(CH_3)_2C(CH_2)_iSO_3^-$—$N^+(CH_3)_2C(CH_2)_iOSO_3^-$ type with i comprised between 1 and 10), or from amino acid functions, particularly such as lysine, ornithine, aspartic or glutamic acid provided with a polymerisable acrylic group such as $CH_2=CHCONH-(CH_2)_j-$ with j comprised between 2 and 5.

In an advantageous embodiment, $R_3$ and/or $R_4$ are a glycosidic group, preferably a monosaccharide or disaccharide or an aminated mono- or di-saccharide, advantageously a mono- or di-saccharide. Preferably, the mono- or di-saccharide is a mono- or di-hexose, particularly of glucose, mannose, galactose, lactose, allose, altrose, idose, lactose, maltose, or cellobiose type, advantageously a glucose, a mannose or a galactose, again preferably a glucose.

Advantageously, $R_5$ is a cyclic hydrocarbon chain ($R_5$ may contain one or two cycles, saturated or not, particularly of cyclohexane or cyclopentane type) or acyclic (linear or branched), saturated or unsaturated (one or more unsaturations), advantageously linear and/or saturated, comprising from 5 to 16 atoms of carbon. Preferably, $R_5$ is a $C_5$-$C_{16}$ alkyl group, preferably $C_8$-$C_{12}$, particularly $C_{11}$, advantageously linear.

More precisely, an advantageous polymer according to the invention comprises at least 75%, preferably at least 80%, advantageously at least 85%, at least 90%, at least 95%, at least 96%, at least 97%, at least 98%, at least 99%, or even 100% of amphiphilic monomers of formula (II):

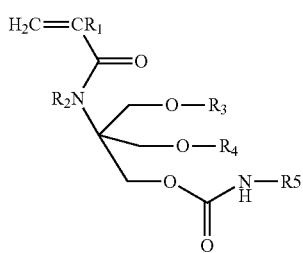

in which $R_1$ and $R_2$ are independently selected from H or a $C_1$-$C_6$ alkyl group, (preferably methyl), $R_3$ and $R_4$ are glycosidic groups as defined above.

$R_5$ is a cyclic hydrocarbon chain ($R_5$ may contain one or two cycles, saturated or not, particularly of cyclohexane, or cyclopentane or aromatic type) or acyclic (linear or branched), saturated or unsaturated (one or more unsaturations), comprising from 5 to 16 carbon atoms as defined above.

Advantageously, $R_3$ and $R_4$, identical or different, preferably identical, are mono- or di-saccharides, preferably mono- or di-hexoses, particularly of glucose, mannose, galactose, lactose, allose, altrose, idose, lactose, maltose, or cellobiose type, preferably a glucose, a mannose or a galactose, advantageously $R_3$ and $R_4$ are glucoses.

Advantageously, $R_5$ is a $C_5$-$C_{16}$ alkyl, preferably $C_8$-$C_{12}$, particularly $C_{11}$, preferably linear.

In an advantageous embodiment:
$R_3$ and $R_4$ are identical and represent a glucose, a mannose or a galactose, preferably a glucose, and
$R_5$ is a $C_5$-$C_{16}$ alkyl, preferably $C_8$-$C_{12}$, particularly $C_{11}$, advantageously linear.

A particularly advantageous polymer according to the invention comprises at least 75%, preferably at least 80%, advantageously at least 85%, at least 90%, at least 95%, at least 96%, at least 97%, at least 98%, at least 99%, or even 100% of amphiphilic monomers of formula (III):

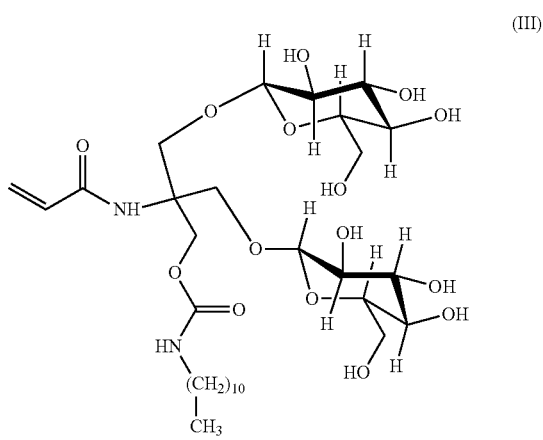

The monomers of formula (I), (II) or (III) as described above are monomers with an acrylic or vinylic unit comprising a hydrophobic fatty chain and two hydrophilic groups (glycosidic groups or zwitterionic residues). They may be synthesised by chemical reactions well known to specialists such as glycosylation, amidification reactions or through use of isocyanate. The synthesis of the monomer of formula (III) is described in detail in the examples. An entirely comparable synthesis route may be used to graft galactoses or mannoses instead of glucoses, and/or to graft another type of fatty chain, particularly any other alkyl chain.

The polymer according to the invention mainly comprises amphiphilic monomers. In an advantageous embodiment, the polymer according to the invention is a homopolymer comprising 100% of monomers of formula (I), (II), or (III) as defined above forming a homogeneous chain, optionally bonded at the head of the chain to another group.

Indeed, the polymers according to the invention may be prepared by polymerisation initiated by radical initiators such as AIBN or benzoyl peroxide in anhydrous solvents heated to a minimum of 60° C. such as THF, acetonitrile or else methanol, the preferred solvent being THF. Advantageously, the size of the polymer during its synthesis is controlled by addition of a chain transfer agent of thiol type, the ratio of concentrations of the latter to the monomer controlling the size of the polymer. The second interest of the presence of this transfer agent is to allow the introduction at the chain end of a specific group capable of being used for its particular properties. Thus, in this case, the polymer according to the invention comprises a specific group at the head of the chain of the polymer. When reference is made to a homopolymer according to the invention, it thus includes the possibility of the presence at the head of the chain of the polymer of a specific distinct group stemming from the chain transfer agent, and which has then been able to be modified.

Particularly, the polymer according to the invention may further comprise at the head of the chain (in other words at one of its ends) a group comprising a thiol function of formula $R_9-S-$, wherein $R_9$ is advantageously selected from:
—$(CH_2)_m$ COOH with m=1 to 11,
—$(CH_2)_m-NH_2$ with m=2 to 11, —(CH₂)ₘ—X—R₁₀ with m=1 to 11; X=O, NH, COO, CONH, S, phosphonate P(O) (O—R₁₀)₂; and R₁₀ selected from H, CH₃, a benzoyl or benzyl group, a fluorescent agent (such as NBD, a derivative of fluorescein or rhodamine, etc.) a biotin, a polysaccharide (particularly a trisaccharide) linear or branched comprising hexoses, a free radical trapping agent such as a nitrone or a cyclic paramagnetic species of nitroxide type.

—(CH₂)ₘ—CONH(CH₂)ₚS—R₁₁ with m comprised between 1 and 10, p comprised between 2 and 11, and R₁₁ selected from H, —C(C₆H₅)₃, a fluorescent agent such as NBD or fluorescein, a free radical trapping agent such as a nitrone or a cyclic paramagnetic species of nitroxide type, an oligomer derivative of an acrylic or vinylic monomer such as methyl acrylate, acrylamide, THAM, vinyl acetate.

—(CH₂)ₘ—CO(OCH₂CH₂)ₓOCO(CH₂)ₚS—R₁₁ with m comprised between 1 and 10, x comprised between 3 and 100, p comprised between 2 and 11, and R₁₁ is as defined above, —(CH₂)₂—(—OCH₂CH₂)_q—O—R₁₀ with q=1 to 100, and R₁₀ is as defined above, —(CH₂)ᵣCONHC(CH₂OR₁₂)₃, —CH₂CONHC(CH₃)(CH₂OR₁₂)₂, or CH₂CONHCH(CH₂OR₁₂)₂ with r comprised between 1 and 11, and R₁₂ is selected from H, a benzyl group or a benzoyl group, a fluorescent agent (such as NBD, a derivative of fluorescein or rhodamine), a biotin, a monosaccharide or a linear or branched polysaccharide, optionally aminated, preferably composed of monomers of mannose, galactose, glucose, sialic acid, glucosamine, galactosamine, and/or mannosamine, a free radical trapping agent such as a nitrone or a cyclic paramagnetic species of nitroxide type.

(CH₂)ₘ P(O) (OR₁₃)₂ with m comprised between 2 and 11, and R₁₃ represents a C₁ to C₁₆ linear alkyl group optionally substituted, a linear hydrocarbon chain comprising 3 to 20 carbon atoms, saturated or unsaturated, optionally substituted in particular by one or more OH groups, advantageously a C₃-C₂₀ linear alkyl group or C₃-C₂₀ linear alkenyl optionally substituted by one or more OH groups (such as phytol for example), or a perfluorinated chain of formula C_tF_{2t+1} (CH₂)ₘ with t comprised between 2 and 10 and m comprised between 2 and 10.

All of these compounds of thiol type are either accessible commercially or easily prepared by simple, high yield chemical reactions.

"C₃-C₂₀ linear alkenyl" is intended to mean a linear hydrocarbon chain comprising 3 to 20 carbon atoms and comprising at least one double bond.

Advantageously, R₉ represents —(CH₂)ᵣCONHC(CH₂OR₁₂)₃, CH₂CONHC(CH₃)(CH₂OR₁₂)₂, or —CH₂CONHCH(CH₂OR₁₂)₂ with r comprised between 1 and 11, wherein R₉ represents H, a benzyl or a benzoyl group, a fluorescent agent (such as NBD, a derivative of fluorescein or rhodamine), a biotin, or a monosaccharide or a polysaccharide, linear or branched, optionally aminated, preferably a compound of monomers of mannose, galactose, glucose, sialic acid, glucosamine, galactosamine, and/or mannosamine.

A particularly preferred chain transfer agent is that where R₉ is (CH₂)₂CONHC(CH₂OH)₃.

In the case where the polymer according to the invention comprises 100% of monomers of formula (I), this then results in a polymer of formula (IV):

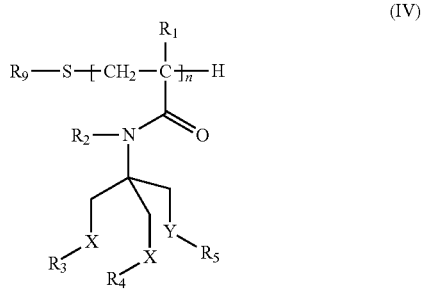

in which R₁ to R₅ and R₉ are as defined above, and n is such that the polymer has an average molar mass comprised between 800 and 100 000, which corresponds to n comprised between 1 and 120, advantageously less than or equal to 50 000 (n less than or equal to 60), preferably between 8000 and 50 000 (n comprised between 1 and 60).

A quite particularly preferred polymer according to the invention is of formula (V)

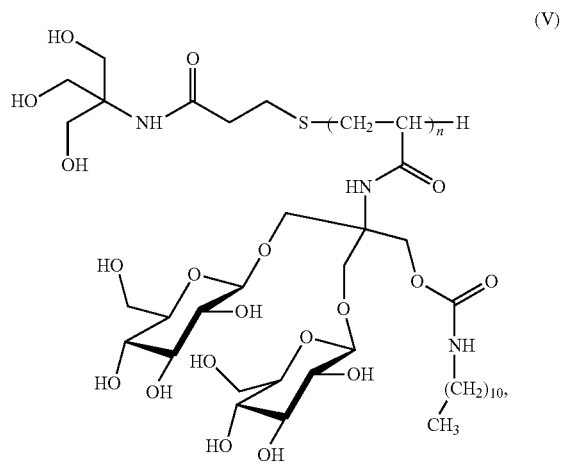

wherein n is comprised between 1 and 120, preferably between 1 and 60.

The invention also relates to a method of preparing an amphiphilic polymer according to the invention, comprising the reaction of a monomer of formula (I), (II) or (III) as described previously with a chain transfer agent in the presence of a radical initiator in an anhydrous solvent at least 60° C.

The chain transfer agent is a compound of thiol type, preferably of formula (VI):

R₉—SH (VI), in which R₉ is as defined above.

The radical initiator may particularly be azobisisobutyronitrile (AIBN) or benzoyl peroxide.

The invention also relates to a water soluble complex of a hydrophobic or amphiphilic compound, advantageously a membrane protein, and an amphiphilic polymer according to the invention. Advantageously, the membrane protein is selected from the group constituted of membrane enzymes, membrane receptors, membrane ion channels, membrane antigens of micro-organisms or tumours, and medicinal proteins (such as particularly antibodies). The complex according to the invention may moreover be in frozen or lyophilised form.

The invention also relates to an aqueous solution having a concentration greater than 1 g/l, advantageously greater than 2 g/l, 3 g/l, or 4 g/l, preferably greater than 5 g/l, 6 g/l, 7 g/l, 8 g/l, 9 g/l, or 10 g/l of one or more complex(es) according to the invention. The concentration is advantageously less than 500 g/l. Preferably the concentration of the solution is between 10 and 500 g/l.

The invention also relates to a product comprising a support and at least one complex according to the invention, said complex being fixed on said support through the amphiphilic polymer according to the invention.

Finally, the invention relates to the use of a complex, of an aqueous solution or of a product according to the invention to detect the presence or the absence in a biological sample of a ligand of said hydrophobic or amphiphilic compound.

EXAMPLES

Example 1

Figure 1:
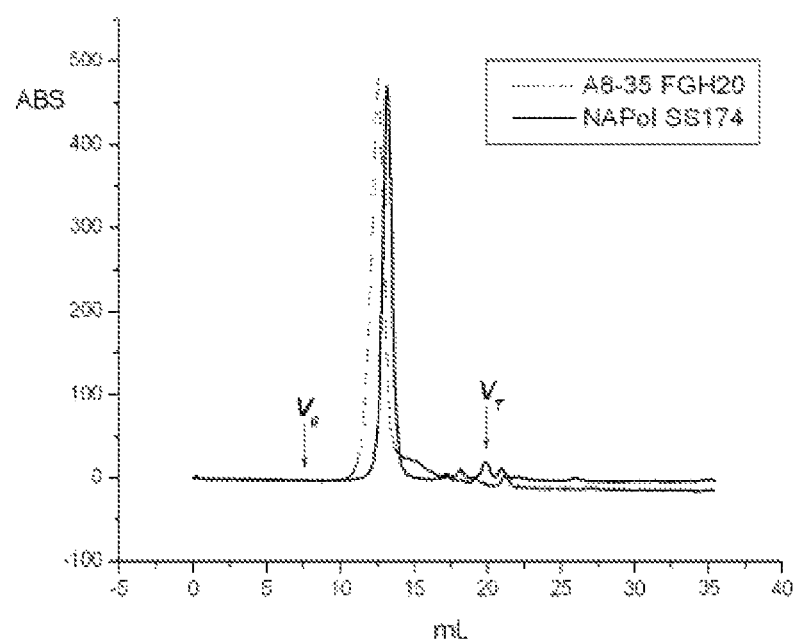
FIG. 1. Estimation by filtration on molecular sieve of the size and the Dispersity of the particles of amphiphilic telomer. One hundred µL of a stock solution of homotelomer (batch SS174) were diluted in 900 µL of Tris/HCl buffer (20 mM Tris, 100 mM NaCl, pH=8.5) and injected into a column of Superose 12 10-300 GL. The elution was carried out with Tris buffer and the detection at 220 nm. Vo and Vr indicate respectively the excluded volume and the total volume of the column (respectively 7.53 and 19.9 mL). The apparent Stokes radius is 2.6 nm. For comparison, a sample of conventional anionic amphipol of A8-35 type was analysed in the same conditions (batch FGH20). The apparent Stokes radius of the particles of A8-35 is 3.15 nm.

Preparation of Homoamphiphilic Polymers 1.1 Synthesis of the diglucosylated acrylamide monomer: Example of N-(1.1-di(O-β-D-glucorpyranosyloxymethyl)-1-(undecyl carbamoyloxymethyl) methyl)acrylamide According to a first method, which is that having generated the monomers having been used in the remainder of the examples, the synthesis takes place in three steps from commercial THAM (which may be obtained with a yield greater than 90% from Tris-(hydroxymethyl)aminomethane), according to the following schema 1.

Schema 1.
First method of synthesizing the diglucosylated acrylamide monomer.

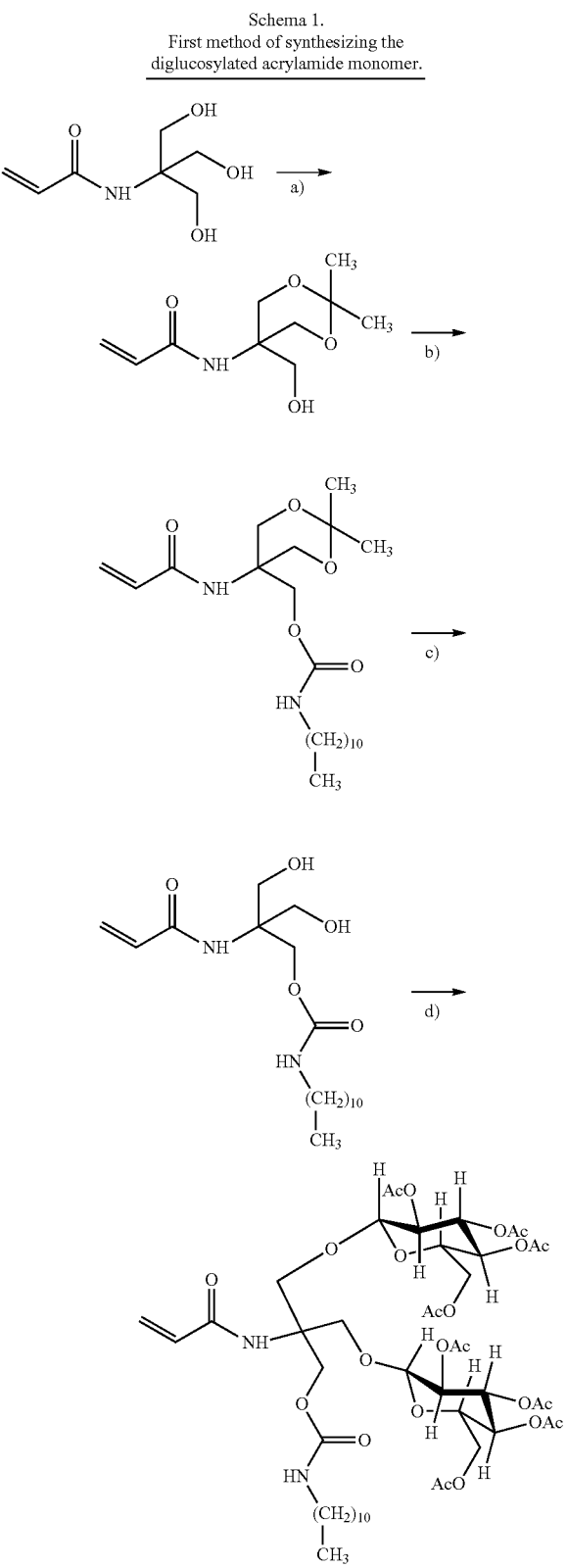

Reagents and reaction conditions: a) $(CH_3)_2C(OCH_3)_2$, $CH_3CN$, apts, 200, R=80%; $CH_3(CH_2)_{10}NCO$, DABCO, toluene, 80° C., R=98%; resin MK-10, 48 h, $CH_2Cl_2$, 84%); $HgCN2$, drierite, toluene, acetobromoglucose (3 equivalents), ))), r=63%.

Synthesis of Isopropylidene THAM

Firstly, two hydroxyl functions are blocked in the form of an isopropylidene group by treating for 24 h THAM with dimethoxypropane in the presence of a catalytic quantity of paratoluene sulphonic acid in acetonitrile at ambient temperature. After normal treatment, the isopropylidene THAM crystallises and is isolated with a yield of 80%.

5-acrylamido-5-undecylcarbamoyloxymethyl-2,2 dimethyl-cyclol, 3 dioxahexane

Isopropylidene THAM (2.64 g, 12.28 mmol, 1.0 equiv.) and 1,4-diaza bicyclo[2,2,2]octane DABCO (4.05 g, 14.74 mmol, 1.2 equiv.) are dissolved in anhydrous toluene and the mixture is heated to reflux for 30 min under argon. Dodecyl isocyanate (2.91 g, 14.74 mmol, 1.2 equiv.) in toluene solution is added drop by drop to the solution maintained at 80° C. After 12 h of stirring, drops of methanol are added and the mixture thrown into ethyl acetate (150 mL). The organic phase is washed with 1N HCl (3×100 mL) and a saturated NaCl solution (2×100 mL), dried on $Na_2SO_4$ and concentrated under vacuum to lead to the compound isopropylidene THAM provided with an undecyl chain bonded by a carbamate group (5.0 g, 12.12 mmol, 98%) in the form of a white powder. $R_f$~0.7, ethyl acetate/cyclohexane (7:3 v/v). $^1$H NMR ($CDCl_3$ δ 7.01 (s, 1H), 6.21 (dd, J=1.6 and 17.0 Hz, 1H), 6.08 (dd, J=10.0 and 17.0 Hz, 1H), 5.65 (dd, J=1.6 and 10.0 Hz, 1H), 4.99 (m, 1H), 4.72 (d, J=12.1 Hz, 2H), 3.62 (d, J=12.0 Hz, 2H), 3.20 (q, J=6.7 Hz, 2H), 1.62 (s, 3H), 1.48 (m, 2H), 1.42 (s, 3H), 1.27 (s, 18H), 0.89 (t, J=6.6 Hz, 3H). $^{13}$C NMR ($CDCl_3$ δ 165.7, 157.6 (CO), 131.4 (CH), 126.5 ($CH_2$), 98.5 (C), 64.9, 60.5 ($CH_2$), 53.5 (C), 43.0, 41.3, 10 31.9, 31.3, 29.8, 29.6, 29.6, 29.5, 29.3, 26.7 ($CH_2$), 26.6 ($CH_3$), 22.7 ($CH_2$), 21.0, 14.1 ($CH_3$).

N-(1,1-(2',3', 4',6'tetra-O-acetyl-β-D-glucopyranosyloxy-methyl)-1-(undecylcarbamoyl oxymethyl)-methyl)-acryl-amide The preceding compound (5.0 g, 12.12 mmol) and the resin MK-10 (30 g) are stirred in dichloromethane (200 mL) for 48 h, the resin is then filtered on a short column of Celite and rinsed with methanol (2×100 mL). The organic phase is concentrated under vacuum to lead to N-(1,1-bishydroxymethyl-1-(undecylcarbamoyl oxymethyl)methyl)-acrylamide (3.8 g, 10.2 mmol, 84%). This compound (2.0 g, 5.37 mmol, 1.0 equiv.), mercury cyanide (2.13 g, 16.10 mmol, 3.0 equiv.) and drierite are mixed in toluene under argon. After 2 minutes of sonication, bromo tetra acetyl glucose TAGB (6.62 g, 16.10 mmol, 3 equiv.) is added and the mixture subjected to sonication for 30 min. The reaction mixture is then filtered on Celite and rinsed with ethyl acetate (100 mL). The organic phases are washed successively with saturated sodium bicarbonate solution (2×100 mL), water (100 mL), 10% potassium iodide solution (4×50 mL), saturated thiosulphate solution (4×50 mL) and water (2×50 mL). The organic phases are dried on $Na_2SO_4$ and concentrated under reduced pressure, the resulting crude product is subjected to flash chromatography, eluted with ethyl acetate/cyclohexane (3:7 v/v) to lead to the expected monomer in the form of a white powder. (3.5 g, 3.39 mmol, 63%). $R_f$~0.35, ethyl acetate/cyclohexane (7:3 v/v). Mp 58.0° C. $[\alpha_D^{25}]$=−12.70 (c, 1, $CH_2Cl_2$). $^1$H NMR ($CDCl_3$) δ 6.92 (s, 1H), 6.24 (dd, 0.7=1.4 and 16.0 Hz, 1H), 6.04 (dd, J=10.0 and 16.9 Hz, 1H), 5.64 (dd, J=1.4 and 10.0 Hz, 1H), 5.3-4.9 (m, 7H), 4.5 (m, 2H), 4.4-3.9 (m, 10H), 3.71 (dt, J=2.4 and 7.3 Hz, 2H), 3.16 (q, J=6.5 Hz, 2H), 2.11, 2.07, 2.05, 2.02 (5 s, 24H), 1.34 (m, 18H), 0.89 (t, J=6.6 Hz, 3H). $^{13}$C NMR ($CDCl_3$) δ 170.8, 170.7, 170.7, 170.2, 169.6, 169.5, 169.5, 169.5, 165.7, 157.2 (CO), 131.3 (CH), 126.6 ($CH_2$), 101.0, 100.8, 77.3, 72.6, 72.5, 71.8, 71.8, 71.1, 68.3, 68.2, (CH), 68.6, 68.3, 68.0, 64.5, 61.7, 60.4 ($CH_2$), 59.6 (C), 41.2, 31.9, 29.8, 29.6, 29.3, 26.8, 26.8, 22.7 ($CH_2$), 21.1, 20.8, 20.8, 20.7, 20.7, 20.6, 20.6, 20.6, 14.2 ($CH_3$). HRMS (ESI+) calculated for $C_{47}H_{72}N_2O_{23}$ ([M+H]+): 1033.4599. Found: 1033.4609 [M+H]+.

According to an alternative method, the synthesis of the acrylamide monomer (N-(1,1-di(-O-β-D-glucopyranosyl oxymethyl)-1-(undecylcarbamoyl oxymethyl)methyl)acrylamide) takes place in two steps from commercial THAM (which may be obtained with a yield greater than 90% from Tris-(hydroxymethyl)aminomethane, according to the following schema 1.

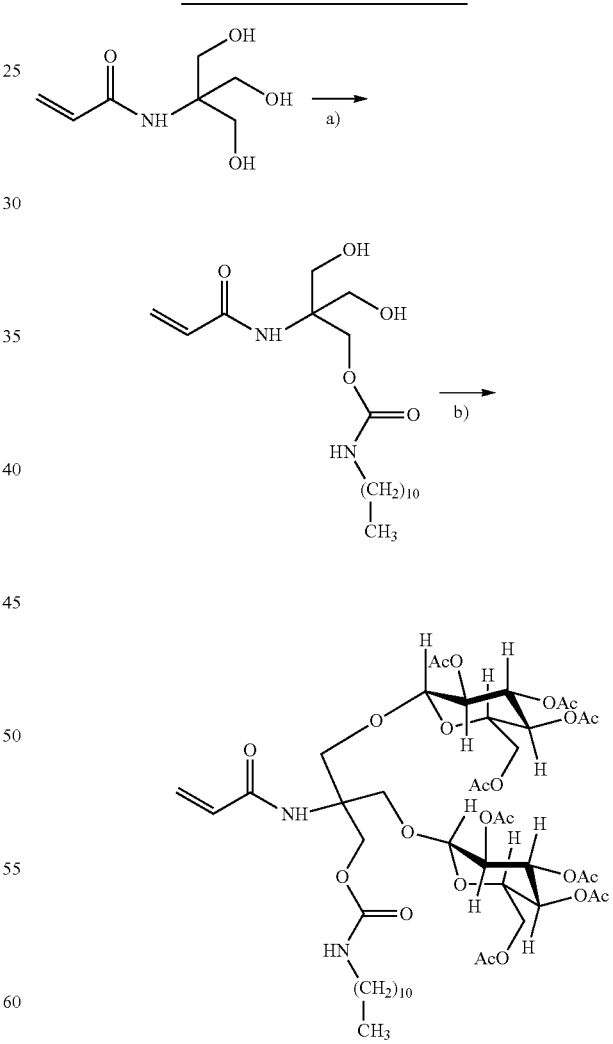

Schema 2.
Second method of synthesizing the diglucosylated acrylamide monomer.

Reagents and reaction conditions: a) THAM (5 equiv), $CH_3(CH_2)_{10}NCO$ (1 equiv.), DABCO (0.5 equiv), DMF, 60° C., 3H, R=80%; b) $HgCN_2$, drierite, toluene, acetobromoglucose (3 equivalents), ))), r=63%

N-1,1-di(hydroxymethyl methyl)-1(undecylcarbamoyl oxymethyl)-methyl)acrylamide To a stirred solution of THAM (21.9 g, 125 mMol, 5 equiv) and diazabicyclo[2,2,2]octane (DABCO) (1.5 g, 13.4 mMol, 0.5 equiv) in 40 mL of DMF heated to 60° C., is added drop by drop under argon atmosphere undecyl isocyanate (5 g, 25 mMol, 1 equiv) solubilised beforehand in 10 mL of methylene chloride. The reaction mixture is maintained at 60° C. up to the total disappearance of the undecyl isocyanate (~30 min). The solvents are then evaporated under reduced pressure and the precipitate taken up with 200 mL of methylene chloride. The suspension is mechanically stirred for 15 min at ambient temperature. The residual precipitate is filtered and again taken up in suspension in 100 mL of methylene chloride then once again filtered. The operation is repeated twice. The remaining precipitate is immediately recrystallised in anhydrous methanol to give 16.5 g of THAM, which can thus be again placed in reaction. The organic phases are combined, washed with 2×50 mL of 1N HCl solution, 2×50 mL of saturated sodium carbonate solution and 2×50 mL of water, dried on sodium sulphate and concentrated under reduced pressure. The crude product is crystallised in a solution of AcOEt/Hexane 2/8 to give N-1,1-di(hydroxymethyl methyl)-1 (undecyl carbamoyloxymethyl)-methyl)acrylamide in the form of a white powder (7.55 g, R=80%). $R_f$~0.5 (ethyl acetate/cyclohexane (8:2 v/v) $^1$H NMR (DMSOd$_6$) δ 7.56 (s, 1H), 7.12 (t, J=5, 1H), 6.36 (dd, J=10 and 17.5 Hz, 25 1H), 6.04 (dd, J=2.2 and 17.5 Hz, 1H), 5.56 (dd, J=2.2 and 10 Hz, 1H), 4.87 (m, 2H), 4.17, (s, 2H), 3.63 (s, 2H), 3.61 (s, 2H), 2.95 (m, 2H), 1.37 (m, 2H), 1.24 (m, 16H), 0.86 (t, J=6.75, 3H). $^{13}$C NMR (DMSOd$_6$) δ 166.5, 156.8, 132.8, 125.5 (CO), 62.6, 61.5, 60.4 (CH$_2$), 31.8, 29.9, 29.5, 29.2, 29.3, 26.7, 22.6, 14.5 (CH$_3$).

N-(1,1-(2 3 4 6'tetra-O-acetyl-ft-D-glucopyranosyloxy-methyl)-1-(undecyl carbamoyloxymethyl)-methyl)-acryl-amide The preceding compound (2.0 g, 5.37 mmol, 1.0 equiv.), mercury cyanide (2.13 g, 16.10 mmol, 3.0 equiv.) and drierite are mixed in toluene under argon. After 2 minutes of sonication, bromo tetra acetyl glucose TAGB (6.62 g, 16.10 mmol, 3 equiv.) is added and the mixture subjected to sonication for 30 min. The reaction mixture is then filtered on Celite and rinsed with ethyl acetate (100 mL). The organic phases are washed successively with saturated sodium bicarbonate solution (2×100 mL), water (100 mL), 10% potassium iodide solution (4×50 mL), saturated thiosulphate solution (4×50 mL) and water (2×50 mL). The organic phases are dried on Na$_2$SO$_4$ and concentrated under reduced pressure, the resulting crude product is subjected to flash chromatography, eluted with ethyl acetate/cyclohexane (3:7 v/v) to lead to the expected monomer in the form of a white powder. (3.5 g, 3.39 mmol, 63%). $R_f$~0.35, ethyl acetate/cyclohexane (7:3 v/v). Mp 58.0° C. [α$_D$$^{25}$]=−12.70 (c, 1, CH$_2$Cl$_2$). $^1$H NMR (CDCl$_3$) δ 6.92 (s, 1H), 6.24 (dd, 0.7=1.4 and 16.0 Hz, 1H), 6.04 (dd, J=10.0 and 16.9 Hz, 1H), 5.64 (dd, J=1.4 and 10.0 Hz, 1H), 5.3-4.9 15 (m, 7H), 4.5 (m, 2H), 4.4-3.9 (m, 10H), 3.71 (dt, J=2.4 and 7.3 Hz, 2H), 3.16 (q, J=6.5 Hz, 2H), 2.11, 2.09, 2.07, 2.05, 2.02 (5 s, 24H), 1.34 (m, 18H), 0.89 (t, J=6.6 Hz, 3H). $^{13}$C NMR (CDCl$_3$) δ 170.8, 170.7, 170.7, 170.2, 169.6, 169.5, 169.5, 169.5, 165.7, 157.2 (CO), 131.3 (CH), 126.6 (CH$_2$), 101.0, 100.8, 77.3, 72.6, 72.5, 71.8, 71.8, 71.1, 68.3, 68.2, (CH), 68.6, 68.3, 68.0, 64.5, 61.7, 60.4 (CH$_2$), 59.6 (C), 41.2, 31.9, 29.8, 29.6, 29.3, 26.9, 26.8, 26.8, 22.7 (CH$_2$), 21.1, 20.8, 20.8, 20.7, 20.7, 20.6, 20.6, 20.6, 14.2 (CH$_3$). HRMS (ESI+) calculated for C$_{47}$H$_{72}$N$_2$O$_{23}$ ([M+H]+): 1033.4599. Found: 1033.4609 [M+H]+.

1.2 Synthesis of NAPol

The synthesis of the telomer (Schema 3) relies on the use of a transfer agent derivative of mercaptopropionic acid provided with a polybenzoylated Tris group. These different benzoyl groups have a strong UV absorption and are located at the end of the polymer chain. Consequently, they enable the exact determination, by measurement of the UV absorption of the final product, of the mass of the telomer and thus the average degree of polymerisation. It should be noted here that the choice of the tribenzoylated function may be taken as an example of the possibilities of introduction (by means of the nature of the transfer agent used) of interesting functions (fluorescein, cholesterol, biotin, nitrones, etc.) and thus of the functionalisation of the end of chain. This functionalisation can also take place after telomerisation through the intermediary of active ester type groups (such as hydroxysuccinimide, paranitro-benzoate, pentafluoro-benzoate, etc.) introduced beforehand on the telogen.

The synthesis of NAPol is resumed in the following schema 3:

Schema 3.
Schematic illustration of the synthesis of the homotelomer.

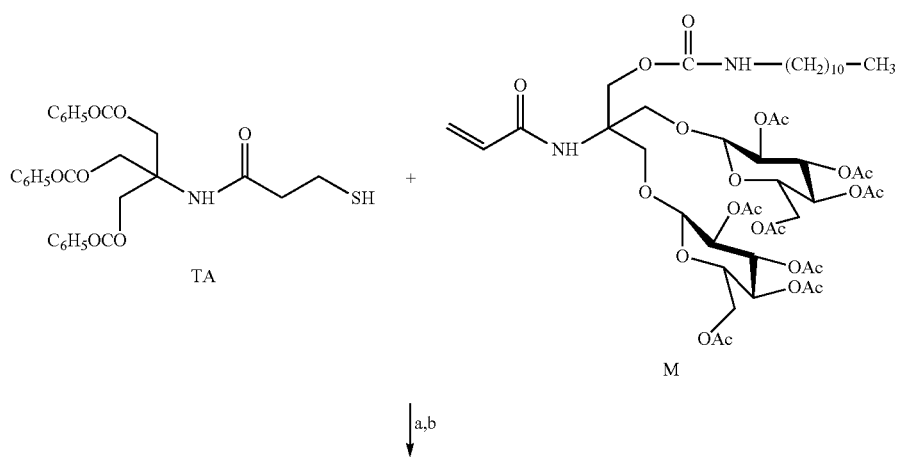

-continued

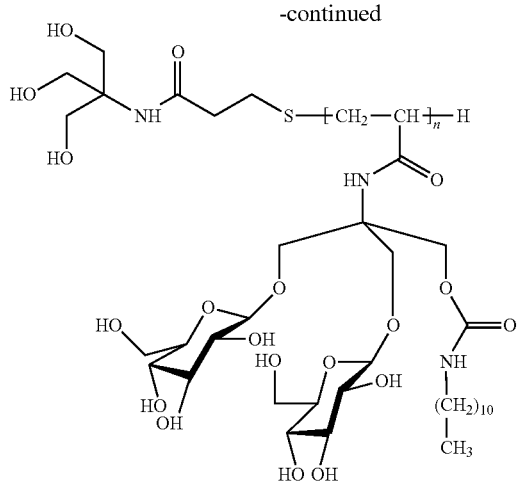

Reagents and conditions: (a) AIBN (0.5 equiv.), THF, Ar, 66° C., 24 h, ~51%; (b) MeONa, MeOH, pH 8-9, ambient temperature, 12h, ~65% after dialysis.

The monomer THAN, N-(1,1-(2',3',4',6'tetra-0-acetyl-β-D-glucopyranosyloxy-methyl)-1-(undecylcarbamoyl oxymethyl)-methyl)-acryl-amide (1.0 g, 0.968 mmol, 40.0 equiv.) is dissolved in THF (15 ml). The solution is degassed by bubbling with argon and heated to reflux for 30 min. The telogen agent TA (12.62 mg, 0.024 mmol, 1.0 equiv.), the synthesis of which has been described previously (Sharma et al), and AIBN (1.98 mg, 0.012 mmol, 0.5 equiv.) dissolved in THF are then added with a micro-syringe. The reaction mixture is stirred at reflux up to the total disappearance of the monomer (~24 h). It is then concentrated under vacuum, and the crude telomer is isolated by size exclusion chromatography (Sephadex® LH-20) by eluting with a MeOH/CH$_2$Cl$_2$ mixture (1:1, v/v), then dried under vacuum. The telomer in protected form is isolated in the form of a white powder (0.524 g, 52%). R$_f$=0.0 ethyl acetate/cyclohexane (6:4 v/v). $^1$H NMR (250 MHz, CDCl$_3$ δ ppm) 0.8 (—CH$_3$ of the alkyl chain), 1.3-1.7 (—CH$_2$) of the alkyl chain), 2.1-2.4 (broad s, —OCOCH$_3$), 3.1 (—NH-vicinal methylene), 4.8-5.3 (m, glucose unit 2H, 3H, 4H, 5H, and 6H), 6.6 (—NH), 7.4-8.1 (three t, C$_6$H$_5$ of the TA).

After determination of the molar mass by $^1$H NMR and UV, the homotelomer (2.0 g, 1.91 mmol) is dissolved in anhydrous methanol (50 mL) under argon atmosphere. A catalytic quantity of sodium methoxide MeONa is added and the solution stirred at ambient temperature over night. The solution is then neutralised with the resin IRC 50 acid (up to pH=8) by stirring for 15 min. After filtration of the resin and evaporation of the solvent, the telomer is subjected to a dialysis with a membrane whose cut off point is 6-8 KDa. The purified polymer is isolated by lyophilisation, it is obtained in the form of a white powder (0.850 15 mg, 65%). $^1$H NMR (250 MHz, DMSO-d$_6$, δ ppm) 0.8 (—CH$_3$ of the alkyl chain), 1.2-1.6 (—CH$_2$)$_{10}$ of the alkyl chain), 3.2 (—NH-vicinal methylene), 4.8-5.2 (m, glucose unit 2H, 3H, 4H, 5H, and 6H), 7.1 (—NH).

The technique developed is universal and can and has already been applied to monomer functions bearing different sugars (galactose and mannose in particular) and to monomers bearing fluorocarbonated chains. It can moreover be easily extended to cotelomers incorporating various types of monomers, whether amphiphilic, hydrophobic or hydrophilic, as we have established previously for mixtures of hydrophilic monomers and hydrophobic.

Example 2

Reproducibility of the Homotelomer Obtained

Different homotelomers have been synthesised, as a function of the relative quantities of monomer and of telogen agent TA. The synthesis conditions and the chemical structure of the synthesised homotelomers are summarised in Table 1.

TABLE 1

Conditions of synthesis and chemical structure of the different NAPols

| | | | Average molar mass $M_w/10^3$ ± 1 × $10^3$ (g · mol$^{-1}$) | |
|---|---|---|---|---|
| | Homotelomer | | | |
| NAPol | Ro$^a$ | DPn$^b$ | Protected | Deprotected |
| SS174 | 20 | 14 | 15 ± 1 | 10 ± 1 |
| SS293 | 20 | 11 | 12 ± 1 | 8 ± 1 |
| SS298 | 40 | 42 | 44.0 ± 1 | 29 ± 1 |
| SS292 | 100 | 90 | 93 ± 2 | 63 ± 2 |
| SS325 | 15 | 16 | 17 ± 2 | 11.3 ± 0.5 |

$^a$Initial Monomer/TA molar ratio,
$^{b,c}$Estimated by UV analysis

In addition, SS298 and SS325 have been synthesised through several different batches with the same precursors and the same conditions. The analysis of the reproducibility of the batches of SS298 is shown in the following Table 2.

TABLE 2

Reproducibility of batches of SS298

| | Homotelomer | | Telomer isolated after Sephadex LH | Average molar mass in acetylated from determined by UV M$_w$/10$^3$ |
|---|---|---|---|---|
| Batches | Ro$^a$ | DPn$^b$ | 20 (mg) | (g · mol$^{-1}$) |
| SS291 | 40 | 34 | 478 | 36 |
| SS294 | 40 | 46 | 532 | 48 |
| SS295 | 40 | 44 | 524 | 46 |

TABLE 2-continued

Reproducibility of batches of SS298

| Batches | Homotelomer Ro[a] | DPn[b] | Telomer isolated after Sephadex LH 20 (mg) | Average molar mass in acetylated from determined by UV $M_w/10^3$ (g·mol$^{-1}$) |
|---|---|---|---|---|
| SS296 | 40 | 55 | 534 | 57 |
| Combined SS298 | 40 | 42 | — | 44 |

[a] Initial Monomer/TA molar ratio,
[b,c] Estimated by UV analysis

The results show a good reproducibility of the batches of amphiphilic homotelomer according to the invention.

Example 3

Characterisation of the Homotelomer and Physical-Chemical Properties

In examples 3 and 4, the novel amphiphilic homotelomers according to the invention are compared with the reference amphipol A8-35, which is a copolymeric anionic amphipol of formula:

Schema 4.
Chemical formula of the amphipol A8-35.

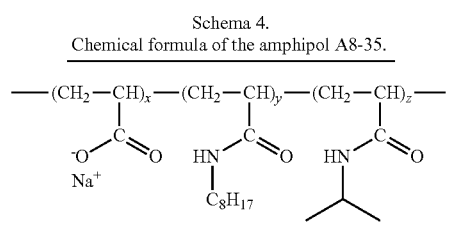

All of the amphiphilic homotelomers according to the invention prepared in example 1 have, after hydrolysis of the ester functions, a solubility in water greater than 100 g/L. The solutions are colourless and foam a little after vigorous stirring. No critical micelle concentration (CMC) or critical aggregation concentration (CAC) can be detected by surface tension measurements, which indicates that, as for the reference amphipol A8-35, the CAC is extremely low. small angle neutron scattering measurements (SANS; not shown) and molecular sieve filtration (SEC; FIG. 1) indicate that this type of telomer combines in aqueous solution to give particles with a total mass of the order of 50 kDa, which substantially corresponds to the association of two telomer molecules and is close to the values determined previously for conventional amphipols of A8-35 type (~40 kDa). The effective radius is comparable to that of the particles dA8-35 (~2.6 vs. ~3.15 nm), as well as the dispersity thereof (FIG. 1). Observed by quasi-elastic light scattering (QLS), the solutions of these telomers appear formed of particles of uniform size of 5-6 nm diameter, in good agreement with the SEC data (Table 3). The size of the particles is not very sensitive to the concentration (Table 3) or to the temperature (Table 4).

TABLE 3

Diameter of the particles of non-ionic homotelomer SS174 at concentrations of 10, 50 and 100 g/L, determined by QLS at different temperatures.

| Sample | Concentration (Gl/$^{-1}$) | $D_H$ (nm) | Mid-height width of the peak a (nm) | Volume distribution of the main peak (in %) |
|---|---|---|---|---|
| SS174 | 10 | 5.8 | 1.4 | 100 |
|  | 50 | 5.9 | 1.5 | 100 |
|  | 100 | 6.3 | 1.6 | 100 |

TABLE 4

Diameter of the particles of non-ionic homotelomer SS298, SS293 and SS292 at a concentration of 50 g/L, determined by QLS at different temperatures.

| Temp. (° C.) | SS298 | | | SS293 | | | SS292 | | |
|---|---|---|---|---|---|---|---|---|---|
|  | $D_H$ (nm) | Mid height peak width (nm) | Volume distribution of the main peak (in %) | $D_H$ (nm) | Mid height peak width (nm) | Volume distribution of the main peak (in %) | $D_H$ (nm) | Mid height peak width (nm) | Volume distribution of the main peak (in %) |
| 2 | 6.14 | 1.77 | 100 | 5.06 | 1.52 | 100 | 6.63 | 1.48 | 99.9 |
| 10 | 5.92 | 1.68 | 100 | 4.91 | 1.47 | 100 | 6.44 | 1.45 | 99.9 |
| 20 | 5.74 | 1.74 | 100 | 4.81 | 1.45 | 100 | 6.0 | 1.69 | 100 |
| 30 | 5.71 | 1.74 | 100 | 4.82 | 1.45 | 100 | 5.93 | 1.71 | 100 |
| 40 | 5.70 | 1.74 | 100 | 4.79 | 1.42 | 100 | 5.92 | 1.69 | 100 |
| 50 | 5.62 | 1.73 | 100 | 4.74 | 1.43 | 100 | 5.9 | 1.76 | 100 |
| 60 | 5.48 | 1.76 | 100 | 4.70 | 1.44 | 100 | a | a | a |
| 70 | 5.47 | 1.79 | 100 | a | a | a | 6.08 | 1.80 | 100 | a: Not determined

Thus, the characterisation of the physical/chemical properties of the non-ionic amphiphilic homotelomers according to the invention shows that these amphipols have properties similar to those of the copolymeric anionic amphipol A8-35.

Example 4

Complexation of the Homotelomer with Membrane Proteins

Amphipols are, by definition, amphiphilic polymers designed to keep membrane proteins soluble and biochemically stable in the absence of detergents. The capacity of the non-ionic homotelomers according to the invention to fulfil these two functions has been tested on two proteins, the transmembrane region of the OmpA protein of the external membrane of *Escherichia coli* (tOmpA) and bacteriorhodopsin (BR). These two proteins are representative of the two major types of structures adopted by transmembrane proteins, the β barrel (tOmpA) and the helix bundle a (BR). Furthermore, BR is a protein that is relatively unstable in detergent solution, and the denaturation of which is easily measured by the release of its cofactor, retinal, which results in a loss of absorption around 564 nm (disappearance of the holoprotein) and the appearance of a peak at 380 nm (due to free retinal).

The data summarised in Table 5 indicate that the two batches of homotelomers tested are practically as efficient as the reference anionic amphipol A8-35 to keep in solution the two proteins after the concentration of the detergent has been lowered below its critical micelle concentration either by dilution with the buffer without detergent (tOmpA), or by adsorption on polystyrene beads (BR): the retention rates in solution vary from 75 to 94%, compared to 89-98% after complexation by 1A8-35, the difference observed for tOmpA (~75% vs. ~90%) being very probably due to the higher density of the complexes formed with the non-ionic amphipols, which causes a slight precipitation during the high speed centrifugation used as test of maintaining in solution. A lower speed was used for the BR, which explains why the difference in maintaining in solution is less important (and the precipitation of the protein in the absence of amphipol-line 2-less complete).

TABLE 5

Capacity of the non-ionic telomers to maintain the membrane proteins in solution.

| Experiment | APols | Weight ratio MP/APol | tOmpA in the supernatant | Native BR in the supernatant |
|---|---|---|---|---|
| 1 | None | 1:0 ([detergent] > CMC) | 98% | 85% |
| 2 | None | 1:0 ([detergent] < CMC) | 5% | 17% |
| 3 | A8-35 | 1:4-1:5 | 89% | 98% |
| 4 | SS174 | 1:4-1:5 | 76% | 93% |
| 5 | SS174 | 1:10 | 75% | 92% |
| 6 | SS298 | 1:5 | n.d. | 93% |
| 7 | SS298 | 1:10 | n.d. | 94% |

To detergent solutions of tOmpA and BR were added a non-ionic homotelomer of the type described in schema 3 above, either of batch SS174 (4-5), or of batch SS298 (6-7), at the indicated mass ratios. After 20 min of incubation, the solutions of tOmpA were diluted with buffer without detergent so as to make the concentration of detergent drop below the cmc, whereas to those of BR were added polystyrene beads (BioBeads), on which the detergent adsorbs. After 2 h of incubation, the solutions were centrifuged for 30 min at 200 000 × g (tOmpA) or 16 000 × g (BR). The fraction of protein present in the supernatant was estimated by measurement of the absorption at 280 nm (tOmpA, BR) or at 554 nm (BR). The controls include the dilution of the protein samples in detergent solution with a solution of detergent above the cmc thereof (1), or with buffer without detergent (2), and an experiment of trapping with the anionic amphipol A8-35 (3), carried out in the same conditions as the experiments 4-7.
n.d.: not determined.

Figure 2:
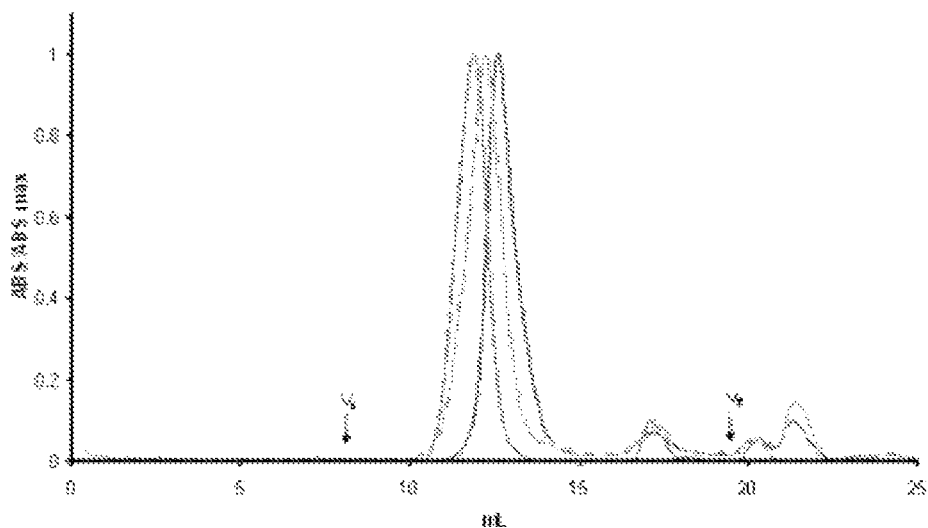
FIG. 2. Estimation by filtration on molecular sieve of the size and the dispersity of tOmpa/amphiphilic telomer complexes. The transmembrane domain (tOmpA) of the protein OmpA of the external membrane of the bacterium *Escherichia coli* was trapped by means of an amphiphilic homotelomer with two different protein/polymer mass ratios, 1:4 (central peak) or 1:10 (right peak) and the samples diluted in Tris/HCl buffer (20 mM Tris, 100 mM NaCl, pH=8.5) injected into a column of Superose 12 10-300 GL. The elution was carried out with Tris buffer and the detection at 280 nm. The peaks have been normalised to the same maximum. Vo and Vr indicate respectively the excluded volume and the total volume of the column. For comparison, a sample of tOmpA trapped with the conventional anionic amphipol of A8-35 type was analysed in the same conditions (left peak). The elution volumes are, from left to right, 11.9, 12.2 and 12.6 mL; the mid height peak widths are respectively 1.00, 1.13 and 0.89 mL.

Preliminary data (not shown) indicate that the non-ionic BR/telomers complexes are of a size comparable (in SEC) to the BR/A8-35 complexes, thus of a small size compatible with their use in biochemistry and biophysics. The same is true for non-ionic tOmpA/telomers complexes, as is clearly apparent in FIG. 2.

Figure 3:
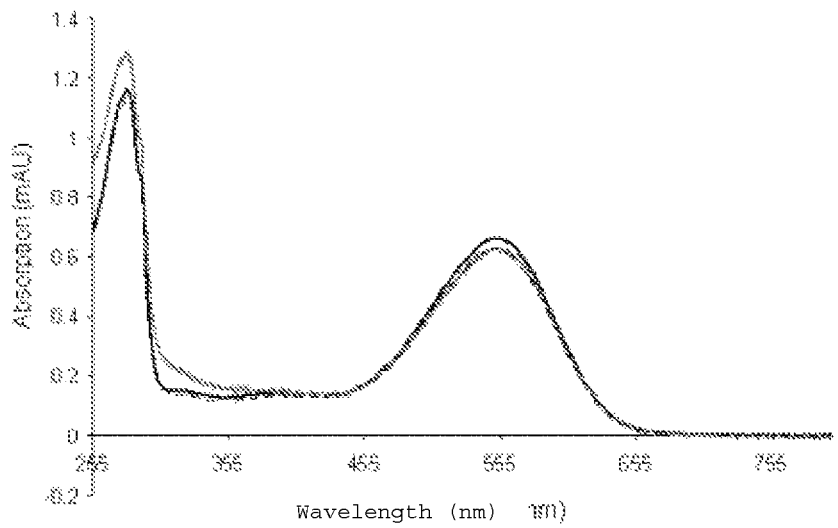
FIG. 3. UV/visible absorption spectra of bacteriorhodopsin after trapping with A8-35 or with non-ionic homotelomers. BR was trapped with a protein/amphipol mass ratio of 1:5, the amphipol being either A8-35 (batch 5 FGH20; in black), or a non-ionic homotelomer (batch SS174: in grey; batch SS298: in black dashes). The spectra were recorded just after the elimination of the detergent (2 h of incubation at 4° C. with BioBeads, centrifugation at 16.000×g for 30 min).

The innocuousness of the non-ionic homotelomers vis-à-vis BR is illustrated (FIG. 3) by the UV/visible spectra of the BR trapped in A8-35 or with each of the two batches of non-ionic homotelomer tested. In the three cases, the ratio of the absorptions at 554 and 280 nm and the absence of a significant peak at 380 nm indicate that the protein is in its native form and has not released its cofactor. (The slightly higher absorbance at 280 nm of the sample trapped with the batch SS174 is due to a slight turbidity).

To summarise, the biochemical tests carried out make it possible to affirm that the non-ionic amphiphilic homotelomers according to the invention a) efficiently trap the membrane proteins and maintain them in solution in the absence of detergent; b) form with them small complexes of a size and of a dispersity comparable with the complexes formed with anionic amphipols such as 1A8-35; and c) stabilise the membrane proteins compared to the detergent solutions. In other words, these polymers have all of the characteristics that make amphipols, and are capable of lending themselves to all the applications of the latter, with the additional advantage that their non-ionic character confers on them, the high reproducibility of their synthesis, and the facility with which it is possible either to graft onto them one single determined functional group per telomeric chain, or to functionalise them in a stochastic manner as performed previously for A8-35.

REFERENCES

Prata, C., Giusti, F., Gohon, Y., Pucci, B., Popot, J.-L. & Tribet, C. (2001). Non-ionic amphiphilic polymers derived from Tris(hydroxymethyl)-acrylamidomethane keep membrane proteins soluble and native in the absence of detergent. *Biopolymers* 56, 77-84:

Sharma, K. S., Durand, G., Giusti, F., Olivier, B., Fabiano, A.-S., Bazzacco, P., Dahmane, T., Ebel, C., Popot, J.-L. & Pucci, B. (2008). Glucose-based amphiphilic telomers designed to keep membrane proteins soluble in aqueous solutions: synthesis and physical-chemical characterization. *Langmuir* 24, 13581-13590.

Tribet, C., Audebert, R. & Popot, J.-L. (1996). Amphipols: polymers that keep membrane proteins soluble in aqueous solutions. *Proc. Natl. Acad. Sci. USA* 93, 15047-15050.

WO 1998/027434
WO 2008/058963

The invention claimed is:

1. An amphiphilic polymer comprising at least 75% of amphiphilic monomers of formula (I):

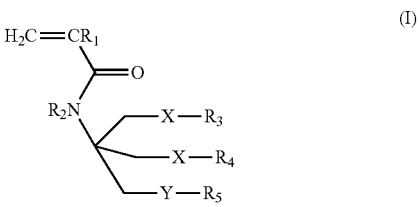

in which
$R_1$ and $R_2$ are independently selected from H or a $C_1$-$C_6$ alkyl group;
X and Y are independently selected from an oxygen atom, a sulphur atom, a carbonyloxy (—(CO)O—) or oxycarbonyl (—O(CO)—) group, a urethane group (—OCONH—), and an amide group of formula (—CONR$_6$—) or (—NR$_6$CO—), wherein R$_6$ is a hydrogen atom or a C$_1$-C$_6$ alkyl;

R$_3$ and R$_4$ are independently selected from:
a) glycosidic groups,
b) zwitterionic residues,
c) poly(oxyalkylene) groups of formula —(O(CH$_2$)$_x$)$_y$—OH, wherein x is comprised between 1 and 6, advantageously x is equal to 2, and y is comprised between 4 and 30,
d) alkyl amide groups of formula —(CH$_2$)$_n$CONR$_7$R$_8$ or —(CH$_2$)$_n$NR$_7$COR$_8$ wherein n is comprised between 1 and 4, R$_7$ and R$_8$ are selected independently from a hydrogen atom, a C$_1$-C$_6$ alkyl group, a glycosidic group, a zwitterionic residue or a poly(oxyalkylene) group of formula —(O(CH$_2$)$_x$)$_y$—OH, wherein x and y are as defined above, R$_5$ is a cyclic or acyclic, saturated or unsaturated, hydrocarbon chain comprising from 5 to 16 carbon atoms, or a hemifluorocarbonated chain of formula C$_t$F$_{2t+1}$(CH$_2$)$_m$ with t comprised between 2 and 10 and m comprised between 2 and 10;

the average molar mass by weight of the polymer being comprised between 800 and 100000.

2. The amphiphilic polymer according to claim 1, wherein R$_1$ and/or R$_2$ are a hydrogen atom.

3. The amphiphilic polymer according to claim 1, wherein X is an oxygen atom.

4. The amphiphilic polymer according to claim 1, wherein Y is a urethane group (—OCONH—).

5. The amphiphilic polymer according to claim 1, wherein R$_3$ and/or R$_4$ are glycosidic groups selected from:
mono- or di-saccharides, or
aminated mono- or di-saccharides.

6. The amphiphilic polymer according to claim 5, wherein R$_3$ and R$_4$ are glucoses.

7. The amphiphilic polymer according to claim 1, wherein R$_5$ is a C$_5$-C$_{16}$ alkyl group.

8. The amphiphilic polymer according to claim 1, wherein it comprises at least 75% of monomers of formula (III):

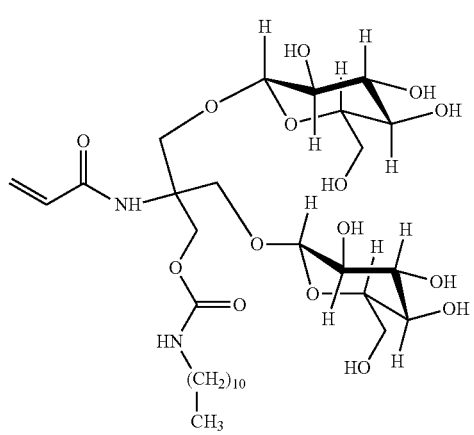

(III)

9. The amphiphilic polymer according to claim 1, wherein it comprises 100% of amphiphilic monomers of formula (I) or (III).

10. The amphiphilic polymer according to claim 1, wherein it further comprises at the head of the chain a group comprising a thiol function of formula R$_9$—S—, R$_9$ being selected from:

—(CH$_2$)$_m$ COOH with m=1 to 11,

—(CH$_2$)$_m$—NH$_2$ with m=2 to 11,

—(CH$_2$)$_m$—OR$_{10}$ with m=1 to 11; X=O, NH, COO, CONH, S, phosphonate P(O)(O—R$_{10}$)$_2$; and R$_{10}$ selected from H, CH$_3$, a benzoyl or benzyl group, a fluorescent agent, a biotin, a linear or branched polysaccharide comprising hexoses, a free radical trapping agent, —(CH$_2$)$_m$—CONH(CH$_2$)$_p$S—R$_{11}$ with m comprised between 1 and 10, p comprised between 2 and 11, and R$_{11}$ is selected from H and —C(C$_6$H$_5$)$_3$, a fluorescent agent, a free radical trap, an oligomer derivative of an acrylic or vinylic monomer, —(CH$_2$)$_m$—CO(OCH$_2$CH$_2$)$_x$OCO(CH$_2$)$_p$S—R$_{11}$ with m comprised between 1 and 10, x comprised between 3 and 100, p comprised between 2 and 11, and R$_{11}$ is selected from H and —C(C$_6$H$_5$)$_3$, —(CH$_2$)$_2$—(—OCH$_2$CH$_2$)$_q$—O—R$_{10}$ with q=1 to 100, and R$_{10}$ is selected from H, CH$_3$, a benzoyl or benzyl group, a fluorescent agent, a biotin, a monosaccharide or a linear or branched polysaccharide, optionally aminated, —(CH$_2$)$_r$CONHC(CH$_2$OR$_{12}$)$_3$, —CH$_2$CONHC(CH$_3$)(CH$_2$OR$_{12}$)$_2$, or CH$_2$CONHCH(CH$_2$OR$_{12}$)$_2$ with r comprised between 1 and 11, and R$_{12}$ is selected from H, a benzyl or a benzoyl group, a fluorescent agent, a biotin, a monosaccharide or a polysaccharide, linear or branched, optionally aminated, —(CH$_2$)$_m$ P(O)(OR$_{13}$)$_2$ with m comprised between 2 and 11, and R$_{13}$ represents a C$_1$ to C$_{16}$ linear alkyl group, optionally substituted, a linear hydrocarbon chain comprising 3 to 20 carbon atoms, saturated or unsaturated, optionally substituted, or a perfluorated chain of formula C$_t$F$_{2t+1}$(CH$_2$)$_m$ with t comprised between 2 and 10 and m comprised between 2 and 10.

11. The amphiphilic polymer according to claim 10, of formula (V):

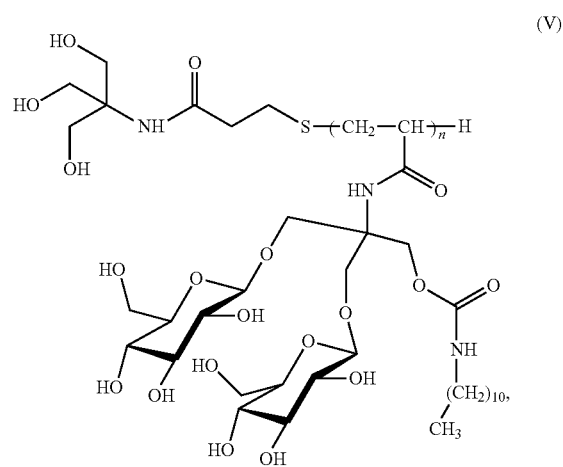

(V)

wherein n is comprised between 1 and 120.

12. A method of preparing the amphiphilic polymer according to claim 1, comprising reacting monomers of formula (I) or (III)

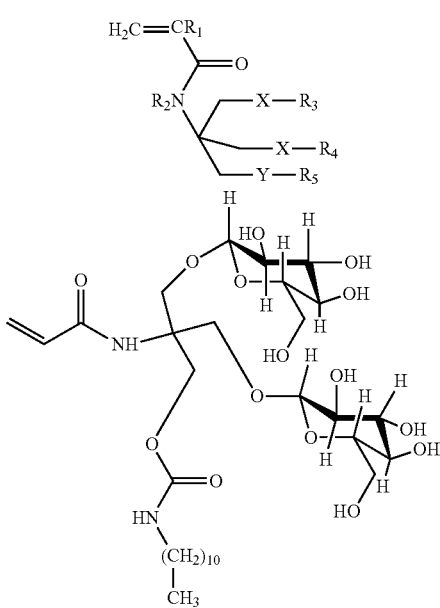

wherein X, Y, $R_1$, $R_2$, $R_3$, $R_4$, and $R_5$ are as defined according to claim 1, with a thiol chain transfer agent in the presence of a radical initiator selected from azobisisobutyronitrile and benzoyl peroxide in an anhydrous solvent selected from tetrahydrofuran, acetonitrile and methanol at at least 60° C.

13. A water soluble complex of a hydrophobic or amphiphilic compound and the amphiphilic polymer according to claim 1.

14. The complex according to claim 13, wherein the hydrophobic or amphiphilic compound is a membrane protein.

15. The complex according to claim 13, in frozen or lyophilised form.

16. An aqueous solution having a concentration greater than 1 g/l of one or more complex(es) according to claim 13.

17. A product comprising a support and at least one complex according to claim 13, said complex being fixed on said support through the amphiphilic polymer according to claim 1.

18. The complex according to claim 14, wherein the membrane protein is selected from the group constituted of membrane enzymes, membrane receptors, membrane ion channels, membrane antigens of micro-organisms or tumours, and medicinal proteins such as antibodies.

19. The aqueous solution according to claim 16, having a concentration between 10 and 500 g/l of one or more complex(es) according to claim 13.

* * * * *